United States Patent
Chen et al.

(10) Patent No.: US 10,769,443 B2
(45) Date of Patent: Sep. 8, 2020

(54) DOMINANT TOOL DETECTION SYSTEM FOR SURGICAL VIDEOS

(71) Applicant: Sony Corporation, Tokyo (JP)

(72) Inventors: Xiaojing Chen, Santa Clara, CA (US); Ko-Kai Albert Huang, Cupertino, CA (US); Ming-Chang Liu, San Jose, CA (US)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/008,826

(22) Filed: Jun. 14, 2018

(65) Prior Publication Data

US 2019/0384980 A1    Dec. 19, 2019

(51) Int. Cl.
*G06K 9/00* (2006.01)
*H04N 5/232* (2006.01)
(Continued)

(52) U.S. Cl.
CPC .......... *G06K 9/00718* (2013.01); *A61B 90/37* (2016.02); *G06K 9/3233* (2013.01); *G06K 9/6267* (2013.01); *G06T 7/70* (2017.01); *H04N 5/23296* (2013.01); *A61B 17/29* (2013.01); *A61B 17/320016* (2013.01); *A61B 2090/372* (2016.02);
(Continued)

(58) Field of Classification Search
CPC ........ A61B 5/7264; A61B 2017/00207; A61B 34/10; B25J 9/1694; G01J 4/00; G06F 3/0213; G06F 1/1694; G06F 2200/1637; G06F 1/1684; G06F 3/03549; G06F 3/03544; G06F 3/04812; G01B 11/245; G01B 11/2433; G01N 23/20058; G01N 21/952; G01N 21/909; G01V 5/00;
(Continued)

(56) References Cited

U.S. PATENT DOCUMENTS 8,108,072 B2    1/2012    Zhao
8,418,073 B2    4/2013    Mohr et al.
(Continued)

FOREIGN PATENT DOCUMENTS

CN       103142313        5/2015
WO    WO2017042812 A2    3/2017

OTHER PUBLICATIONS

Jin et al., Tool Detection and Operative Skill Assessment in Surgical Videos Using Region-Based Convolutional Neural Networks, 2017, Standford University, 5 pages. (Year: 2017).*
(Continued)

*Primary Examiner* — Hung Q Dang
(74) *Attorney, Agent, or Firm* — Trellis IP Law Group, PC

(57) ABSTRACT

Implementations generally relate to detecting dominant tools in surgical videos. In some implementations, a method includes receiving at least one image frame. The method further includes detecting one or more objects in the at least one image frame. The method further includes classifying the one or more objects into one or more tool classifications, where the one or more objects are tools. The method further includes determining a handedness of the one or more tools. The method further includes determining a dominant tool from the one or more tools based at least in part on the one or more classifications of the one or more tools and based at least in part on the handedness of the one or more tools.

14 Claims, 10 Drawing Sheets

(51) Int. Cl.
| | |
|---|---|
| *G06K 9/62* | (2006.01) |
| *G06K 9/32* | (2006.01) |
| *G06T 7/70* | (2017.01) |
| *A61B 34/20* | (2016.01) |
| *A61B 90/00* | (2016.01) |
| *A61B 17/29* | (2006.01) |
| *A61B 17/32* | (2006.01) |

(52) U.S. Cl.
CPC ..... *G06K 9/6215* (2013.01); *G06K 2209/057* (2013.01); *G06T 2207/10016* (2013.01)

(58) Field of Classification Search
CPC ......... F42B 35/00; B25B 13/56; B07C 5/342; B07C 5/10; B07C 5/3422; B64C 2201/12
See application file for complete search history.

(56) References Cited

U.S. PATENT DOCUMENTS

| | | | | |
|---|---|---|---|---|
| 2006/0058616 | A1* | 3/2006 | Marquart | A61B 90/94 600/407 |
| 2009/0245600 | A1* | 10/2009 | Hoffman | A61B 1/00039 382/128 |
| 2010/0228264 | A1* | 9/2010 | Robinson | A61B 18/1206 606/130 |
| 2012/0226150 | A1* | 9/2012 | Balicki | A61B 5/0066 600/424 |
| 2013/0038707 | A1 | 2/2013 | Cunningham | |
| 2013/0288214 | A1 | 10/2013 | Kesavadas | |
| 2014/0005484 | A1* | 1/2014 | Charles | A61B 17/02 600/201 |
| 2014/0160015 | A1* | 6/2014 | Ogawa | B25J 13/02 345/156 |
| 2016/0007827 | A1 | 1/2016 | Frimer et al. | |
| 2018/0014904 | A1* | 1/2018 | Yu | A61F 9/007 |
| 2018/0047553 | A1* | 2/2018 | Richardson | A61B 10/0283 |
| 2018/0064499 | A1* | 3/2018 | Itkowitz | A61B 34/25 |
| 2018/0065248 | A1* | 3/2018 | Barral | A61B 34/25 |
| 2018/0092699 | A1* | 4/2018 | Finley | A61B 34/20 |
| 2018/0092700 | A1* | 4/2018 | Itkowitz | A61B 90/36 |
| 2018/0271603 | A1* | 9/2018 | Nir | A61B 1/3132 |
| 2018/0325604 | A1* | 11/2018 | Atarot | A61B 5/7425 |
| 2019/0045170 | A1* | 2/2019 | Sugie | A61B 90/37 |
| 2019/0046278 | A1* | 2/2019 | Steinle | A61B 34/30 |

OTHER PUBLICATIONS

David Bougeta, et al.; "Vision-Based and Marker-Less Surgical Tool Detection and Tracking: a Review of the Literature"; Medicis team, INSERM U1099, Universit de Rennes 1 LTSI, 35000 Rennes, France bCenter for Medical Image Computing. University College London, WC1E 6BT London, United Kingdom; Sep. 13, 2016.

Suren Kumar, et al.; "Product of Tracking Experts for Visual Tracking of Surgical Tools"; State University of New York (SUNY) at Buffalo; Aug. 17-20, 2013 http://ieeexplore.ieee.org/document/6654037/.

Bou Get David et al: "Detecting Surgical Tools by Modelling Local Appearance and Global Shape", IEEE Transactions on Medical Imaging, IEEE Servi Ce Center, Piscataway, NJ, us, vol. 34, No. 12 Dec. 1, 2015 (Dec. 1, 2015), pp. 2603-2617.

Max Allan et al: "Toward Detection and Localization of Instruments in Minimally Invasive Surgery", IEEE Transactions on Biomedical Engineering, IEEE Service Center, Piscataway, NJ, USA, vol. 60, No. 4, Apr. 1, 2013 (Apr. 1, 2013), pp. 1050-1058.

Wesierski Daniel et al: "Instrument detection and pose estimation with rigid part mixtures model in video-assisted surgeries", Medical Image Analysis, Oxford University Press, Oxofrd, GB, vol. 46, Mar. 30, 2018 (Mar. 30, 2018), pp. 244-265.

PCT/IB2019/054494—Notification of Transmittal of the International Search Report and the Written Opinion.

\* cited by examiner

DOMINANT TOOL DETECTION SYSTEM FOR SURGICAL VIDEOS

CROSS REFERENCE TO RELATED APPLICATIONS

This application is related to the following application, U.S. patent application Ser. No. 16/008,784, entitled "Tool Handedness Determination For Surgical Videos" filed Jun. 14, 2018, which is hereby incorporated by reference as if set forth in full in this application for all purposes.

BACKGROUND

Computer-assisted surgery uses computer technology for guiding or performing medical procedures such as procedures involving endoscopy, laparoscopy, etc. During surgery, a surgeon may need to use various tools to perform surgery. A camera and monitor can help a surgeon to manipulate multiple surgical tools using robotic arms. However, it can be difficult to view surgical tools well on a monitor during surgery.

SUMMARY

Implementations generally relate to detecting dominant tools in surgical videos. In some implementations, a system includes one or more processors, and includes logic encoded in one or more non-transitory computer-readable storage media for execution by the one or more processors. When executed, the logic is operable to perform operations including receiving at least one image frame; detecting one or more objects in the at least one image frame; classifying the one or more objects into one or more tool classifications, where the one or more objects are tools; determining a handedness of the one or more tools; and determining a dominant tool from the one or more tools based at least in part on the one or more classifications of the one or more tools and based at least in part on the handedness of the one or more tools.

With further regard to the system, in some implementations, the one or more tool classifications indicate types of tools. In some implementations, the one or more tool classifications indicate tool functions. In some implementations, the logic when executed is further operable to perform operations including generating a visual indicator for the one or more tools, and demarcating each of the one or more tools in the at least one image. In some implementations, the logic when executed is further operable to perform operations including labeling each tool in the at least one image with a type of tool. In some implementations, the logic when executed is further operable to perform operations including performing the determining of the dominant tool in real-time. In some implementations, the logic when executed is further operable to perform operations including controlling a camera based at least in part on the determining of the dominant tool.

In some embodiments, a non-transitory computer-readable storage medium with program instructions thereon is provided. When executed by one or more processors, the instructions are operable to perform operations including receiving at least one image frame; detecting one or more objects in the at least one image frame; classifying the one or more objects into one or more tool classifications, where the one or more objects are tools; determining a handedness of the one or more tools; and determining a dominant tool from the one or more tools based at least in part on the one or more classifications of the one or more tools and based at least in part on the handedness of the one or more tools.

With further regard to the computer-readable storage medium, in some implementations, the one or more tool classifications indicate types of tools. In some implementations, the one or more tool classifications indicate tool functions. In some implementations, the instructions when executed are further operable to perform operations including generating a visual indicator for the one or more tools, and demarcating each of the one or more tools in the at least one image. In some implementations, the instructions when executed are further operable to perform operations including labeling each tool in the at least one image with a type of tool. In some implementations, the instructions when executed are further operable to perform operations including performing the determining of the dominant tool in real-time. In some implementations, the instructions when executed are further operable to perform operations including controlling a camera based at least in part on the determining of the dominant tool.

In some implementations, a method includes receiving at least one image frame. The method further includes detecting one or more objects in the at least one image frame. The method further includes classifying the one or more objects into one or more tool classifications, where the one or more objects are tools. The method further includes determining a handedness of the one or more tools. The method further includes determining a dominant tool from the one or more tools based at least in part on the one or more classifications of the one or more tools and based at least in part on the handedness of the one or more tools.

With further regard to the method, in some implementations, the one or more tool classifications indicate types of tools. In some implementations, the one or more tool classifications indicate tool functions. In some implementations, the method further includes generating a visual indicator for the one or more tools, and demarcating each of the one or more tools in the at least one image. In some implementations, the method further includes including labeling each tool in the at least one image with a type of tool. In some implementations, the method further includes performing the determining of the dominant tool in real-time.

A further understanding of the nature and the advantages of particular implementations disclosed herein may be realized by reference of the remaining portions of the specification and the attached drawings.

DETAILED DESCRIPTION

Implementations described herein detect dominant tools in surgical videos. As described in more detail herein, a system identifies the dominant tool in an image frame of a video stream in real-time. In various implementations, the dominant tool is a tool with primary functionality (e.g., cut, burn, etc.). Non-dominant tools may be referred to as assistive tools. The system identifies the dominant tool using tool classification results and handedness estimation.

In some implementations, a system receives an image frame. In various implementations, the image frame may be one of a series of image frames of a video stream. The system then detects one or more objects in the image frame and classifies the objects into one or more tool classifications. In various implementations, the objects are surgical tools. The system determines the handedness of the tools. The system determines the dominant tool from the one or more tools based at least in part on the classifications of the tools and the handedness of the tools. The handedness of all presented tool plays an important role in dominant tool identification.

In some implementations, a system receives at least one image frame of a plurality of image frames. The system then detects one or more objects in the at least one image frame, and classifies the one or more objects into one or more tool classifications, where the one or more objects are tools. The system also determines, for each tool, if the tool is assistive or non-assistive. The system then determines, for each tool, a handedness of the tool.

A described in more detail herein, during the surgery, implementations automatically move a camera such that it follows the dominant surgical tool to relieve some burden for the surgeon. Implementations automatically control the camera manually to ensure that the region of interest is located at the center of the field of view of the camera.

Figure 1:
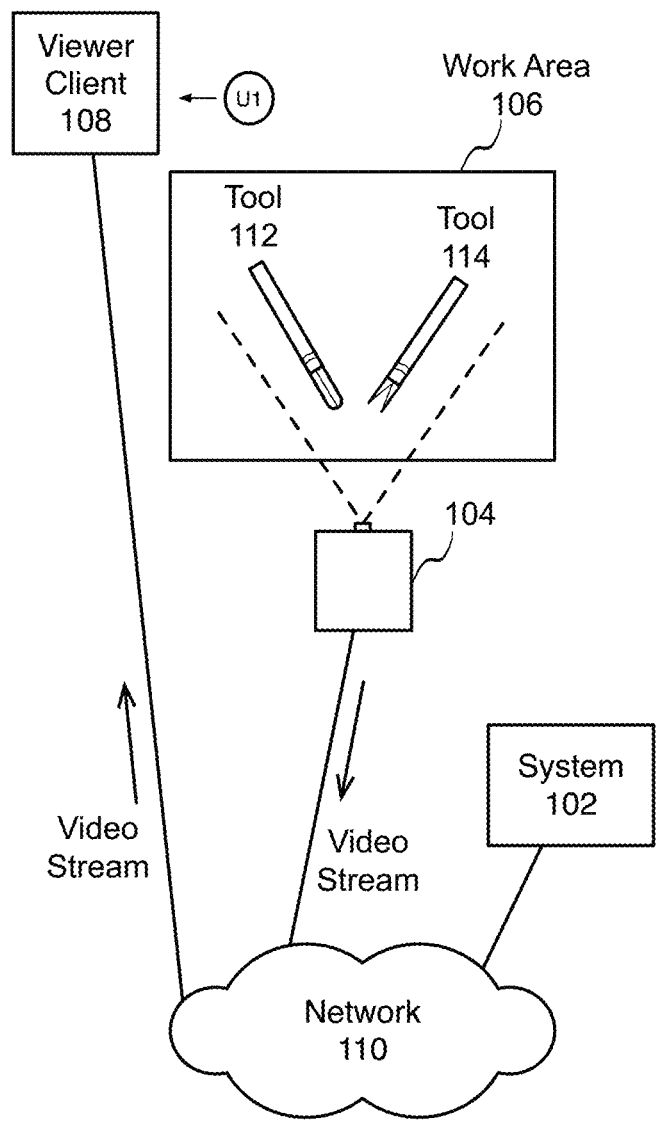
FIG. 1 illustrates a block diagram of an example work environment, which may be used for implementations described herein.

FIG. 1 illustrates a block diagram of an example work environment 100 which may be used for implementations described herein. Shown is a system 102, which performs various implementations described herein. System 102 controls a camera 104, which captures video of a work area 106. System 102 causes camera 104 to send a video stream from camera 104 to viewer client 108 via a network 110. As described in more detail herein, system 102 analyzes the characteristics of tools 112 and 114, which are captured by camera 104.

Figure 2:
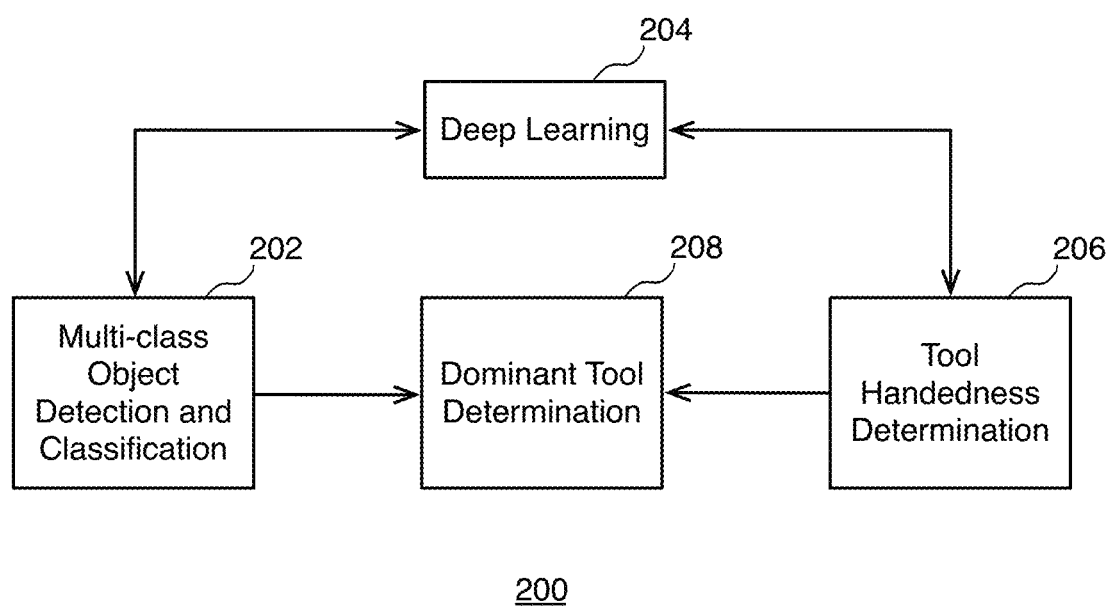
FIG. 2 illustrates an example flow diagram for analyzing tools, according to some implementations.

FIG. 2 illustrates an example flow diagram for analyzing tools, according to some implementations. As shown, at block 202, a system such as system 102 of FIG. 1 performs multi-class object detection and classification. As described in more detail herein, system 102 detects and classifies objects in an image frame. For example, system 102 may detect tools 112 and 114 in an image frame captured by camera 104. At block 204, system 102 may employ deep learning techniques to classify tools. At block 206, system 102 determines the handedness of the tools. For example, system 102 determines if a particular tool is used by a user's right hand or left hand. System 102 may also employ deep learning techniques to determine the handedness of the tools, at block 204. System 102 utilizes deep learning network for tool classification and for determining handedness, which provides a light-weight model for accuracy and speed.

At block 208, system 102 determines which of the tools is the dominant tool. In various implementations, the dominant tool is a primary tool used. Other tools may be referred to as assistive tools in that they assist the user in a primary task using the dominant tool. For example, in a surgical context, a dominant tool may be a clipper that is used to cut tissue of a patient. Further, the dominant tool is typically handled by the dominant hand of a user. A non-dominant tool may be an assistive tool such as grasper, which the user may use to grab particular tissue to pull away from tissue to be cut by the clipper. Further example implementations directed to these steps are described in more detail herein.

Detecting and identifying the dominant tool (e.g., dominant surgical tool) in real-time is beneficial for various natural user interfaces. For example, given the position of dominant tool, a camera can automatically move towards the tool such that the tool is re-centered. This provides a better view for the user (e.g., doctor, etc.). In various implementations, in order to locate the dominant tool in every frame of a video, different types of models may be trained. As such, all the predictions may be combined in a systematical way to produce the final results.

Figure 3:
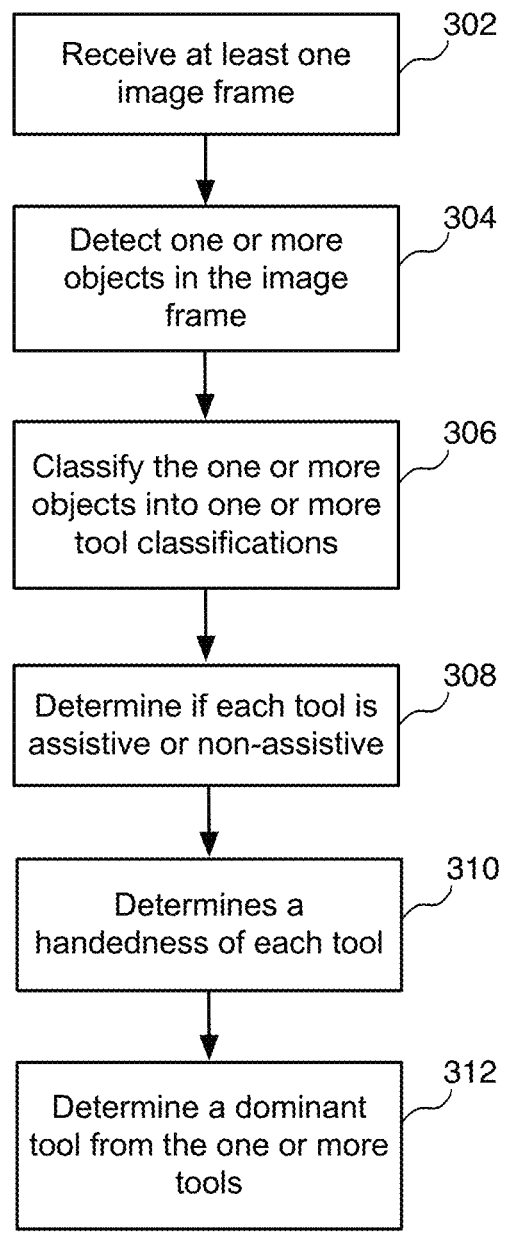
FIG. 3 illustrates an example flow diagram for determining characteristics of tools including handedness of tools and a dominant tool, according to some implementations.

FIG. 3 illustrates an example flow diagram for determining characteristics of tools including handedness of tools and a dominant tool, according to some implementations. As described in more detail below, the system performs various functions including determining the handedness of each tool and determining the dominant tool. Referring to both FIGS. 2 and 3, a method is initiated at block 302, where the system such as system 102 receives at least one image frame. In various implementations, the received image frame is from a sequence of image frames of a video stream.

At block 304, system 102 detects one or more objects in the received image frame. In various implementations, system 102 may use object recognition techniques to detect objects in the received image.

Figure 4:
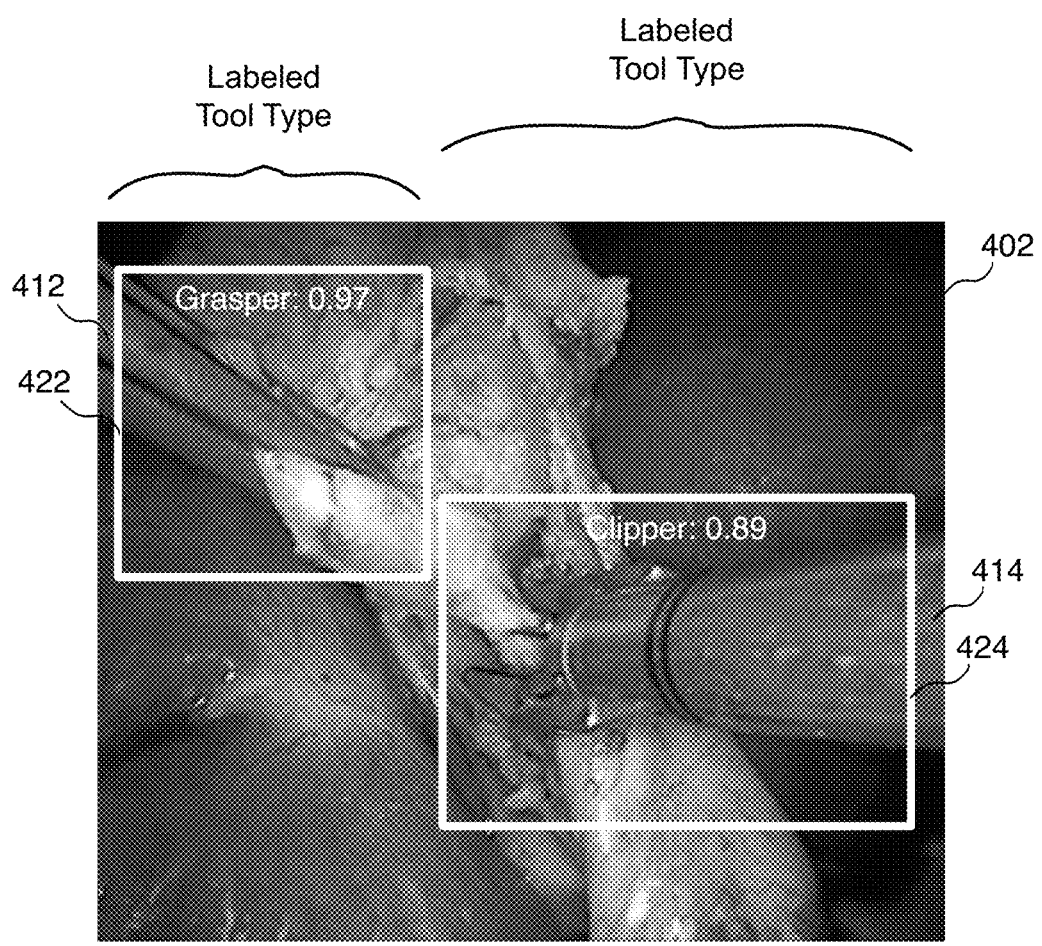
FIG. 4 illustrates example screen shot showing two tools and labels indicating the types of the tools, according to some implementations.

FIG. 4 illustrates example screen shot 400 showing two tools and labels indicating the types of the tools, according to some implementations. Shown is an image frame 402 and objects 412 and 414, which are captured and shown in image frame 402. Other aspects of FIG. 4 are described in more detail below in connection with the following steps.

At block 306, system 102 classifies the one or more objects into one or more tool classifications, where the one or more objects are tools. In this particular example, the tools are surgical tools.

In various implementations, the one or more tool classifications indicate the types of tools, including the tool functions. For example, referring to FIG. 4, the system classifies object 412 as a grasper tool or grasper. As such, object 412 may be referred to as tool 412 or grasper 412. Similarly, the system classifies object 414 as a clipper tool or clipper. As such, object 414 may be referred to as tool 414 or clipper 414.

While various implementations are described in the context of example tools being a grasper and a clipper, these implementations and others also apply to various other types of tools. For example, tools may include cutting or dissecting instruments such as scalpels, scissors, saws, etc. Tools may include bipolar forceps and irrigators. Tools may include grasping or holding instruments such as smooth and toothed forceps, towel clamps, vascular clamps, organ holders, etc. Tools may include hemostatic instruments such as clamps, hemostatic forceps, atraumatic hemostatic forceps, etc. Tools may include retractor instruments such as C-shaped laminar hooks, blunt-toothed hooks, sharp-toothed hooks, grooved probes, tamp forceps, etc. Tools may include tissue unifying instruments and materials such as needle holders, surgical needles, staplers, clips, adhesive tapes, etc. The particular tools detected may vary, and will depend on the particular implementation. While implementations are described herein in the context of surgical tools, these implementations and others may also apply to other tools (e.g., non-surgical tools).

In various implementations, system 102 generates a visual indicator for the one or more tools. System 102 then demarcates each of the one or more tools in the at least one image. For example, referring still to FIG. 4, shown is a bounding box 422 or box 422, which is a visual indicator that demarcates grasper 412. Also shown is a bounding box 424 or box 424, which is a visual indicator that demarcates clipper 414. Boxes 422 and 424 are shown as squares in this example. The actual shape of the visual indicators may be any shape. For example, in some implementations, the visual indicators may follow the general shape of the tools. In various implementations, boxes 422 and 424 and associated labels superimposed in real-time over the video frames for the user to view. This helps the user to know which tools are being viewed on the display. In some implementations, system 102 may enable the user to turn the visual indicators off. Even with visual indicators turned off, system 102 may use information collected to other purposes, such as automatically adjusting the camera to focus on particular tools (e.g., the dominant tool, etc.).

In various implementations, system 102 labels each tool in the at least one image with a type of tool. As shown in FIG. 4, system 102 may label each tool with text (e.g., "Grasper," "Clipper," etc.).

In various implementations, for each object, system 102 identifies features of each of the tools, where the features may include one or more of shape, orientation, and color.

In some implementations, system 102 determines the shape of each tool. For example, clippers may have two opposing blades with a particular shape for cutting. A grasper may also have opposing arms with a particular shape for grasping.

In some implementations, system 102 determines the position of each tool. For example, clippers may be positioned at an upright position in order to cut tissue, and graspers may be positioned at an angled position in order to pull tissue.

In some implementations, system 102 determines the color of each tool. For example, clippers may have a particular color (e.g., red, etc.). Graspers may have a different color (e.g., blue, etc.). In various implementations, system 102 utilizes a deep learning network to classify the objects into the various tool classifications. In some implementations, system 102 uses a classifier that is trained with known features learned by the deep learning network. System 102 uses the known features to determine the type of tool or tool classification based on the features that system 102 recognizes in the image frame.

System 102 compares the features to known features of known tools. System 102 then matches the one or more features to the known features of the known tools. In various implementations, system 102 stores information on the known features in a suitable storage location. Any new information may be used to help to identify features of newly detected tools and to help classify those tools. System 102 then classifies the one or more objects into the one or more tool classifications based on the matching.

The particular features that system 102 analyzes may vary, and will depend on the particular implementations. For example, other features may include the shape of each handle, the length of each handle, etc.

In various implementations, system 102 determines a type confidence score, where the type confidence score indicates an accuracy level of the classifying of the one or more objects into the one or more tool classifications. In some implementations, the type confidence score is based on how closely system 102 can match the detected features of a given tool to known features. In some implementations, the more features that system 102 can match, the system 102 gives a higher type confidence score. For example, if system 102 matches several features (e.g., shape, position, color, etc.), system 102 may give a higher type confidence score (e.g., 0.97). If system 102 matches fewer features (e.g., shape and position), system 102 may give a lower type confidence score (e.g., 0.89). In these examples, the type confidence scores may be in a range of 0 to 1. Other scoring conventions are also possible, depending on the particular implementation. For example, the type confidence score may be a percentage (e.g., 0% to 100%). In some implementations, system 102 may indicate the percentage as shown in FIG. 4.

Referring still to FIG. 3, At block 308, the system determines, for each tool, if the tool is assistive or non-assistive. In various implementations, system 102 determines if the tool is assistive or non-assistive is based at least in part on the type of tool. For example, a tool that is non-assistive such as clippers is typically manipulated with the dominant hand, and a tool that is assistive such as graspers is typically manipulated with the non-dominant hand. As such, if the system detects that a non-assistive tool such as a clipper is on the right, system 102 determines that clipper is being manipulated by the right hand. In some implementations, system 102 may enable the user to enter whether a tool is assistive or non-assistive in order to provide system 102 with more information.

At block 310, the system determines, for each tool, a handedness of the tool. In various implementations, system 102 utilizes a deep learning network to determine the handedness of each tool. In some implementations, system 102 uses a classifier that is trained with features learned by the deep learning network to predict the handedness of each tool. In various implementations, system 102 determines the handedness in real-time with high computational efficiency. In various implementations, system 102 determines the handedness of a particular tool based at least in part on deep learning.

In various implementations, system 102 determines the handedness confidence score, where the handedness confidence score indicates an accuracy level of the determining of the handedness. In some implementations, the handedness confidence score is based at least in part on how accurately system 102 can determine the handedness of a given tool. In some implementations, the more information system 102 has to determine the handedness, the higher type confidence score system 102 may give. For example, if the tool in the image provides a significant signal in one orientation, system 102 may give it a higher handedness confidence score (e.g., 0.99). Otherwise, if the tool is in front of a cluttered background, no significant orientation can be detected, then system 102 may give it a lower handedness confidence score. In these examples, the type confidence scores may be in a range of 0 to 1. Other scoring conventions are also possible, depending on the particular implementation. For example, the type confidence score may be a percentage (e.g., 0% to 100%). In some implementations, system 102 may indicate the percentage as shown in FIG. 5.

Figure 5:
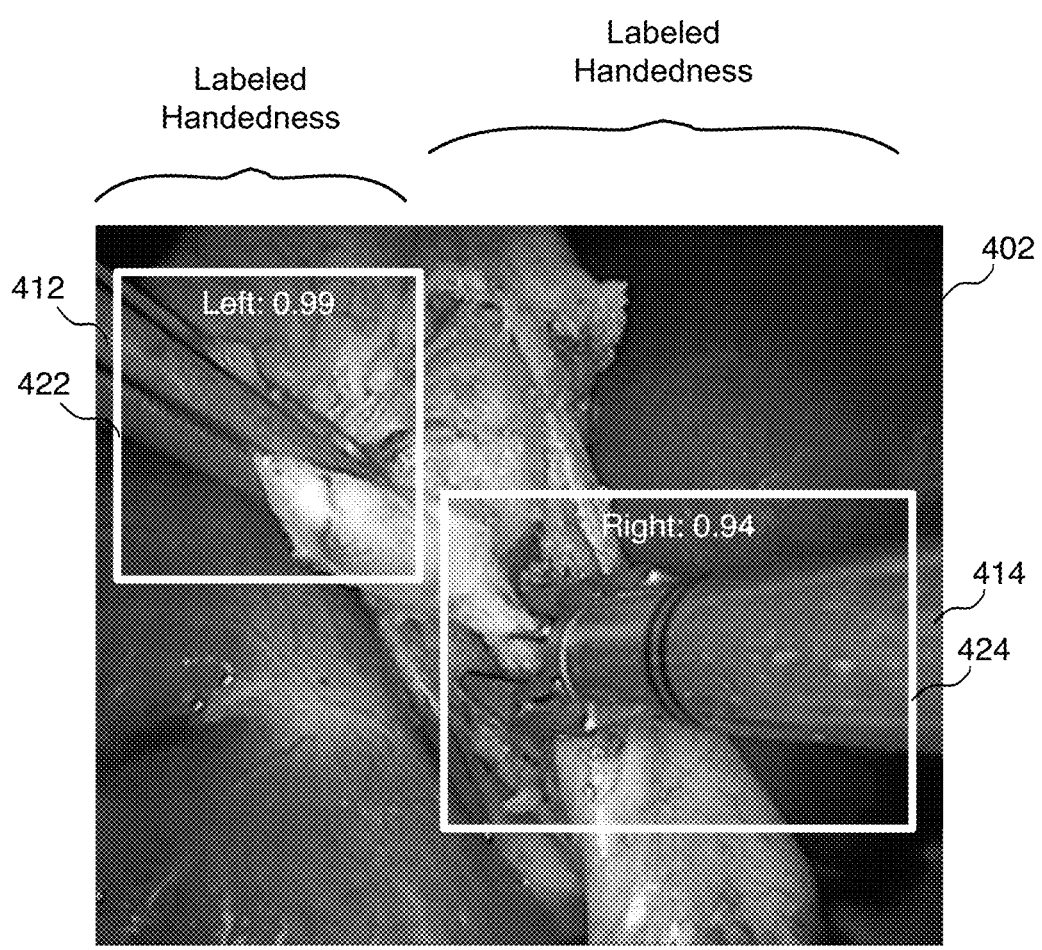
FIG. 5 illustrates example screen shot showing two tools and labels indicating the handedness of the tools, according to some implementations.

FIG. 5 illustrates example screen shot 500 showing two tools and labels indicating the handedness of the tools, according to some implementations. Shown is image frame 402 and objects 412 and 414, which are captured and shown in image frame 402. Also shown is box 422, which is a visual indicator that demarcates grasper 412, and box 424, which is a visual indicator that demarcates clipper 414. In various implementations, system 102 labels each tool in image frame 402 with the handedness of each tool. For example, as shown, system 102 may label each tool with text to indicate if the tool is being used with the left hand or the right hand (e.g., "Left," "Right," etc.).

At block 312, the system determines a dominant tool from the one or more tools based at least in part on the one or more classifications of the one or more tools and based at least in part on the handedness of the one or more tools. In various implementations, system 102 performs the determining of the dominant tool in real-time with high computational efficiency. As indicated herein, the dominant tool is a primary tool used. For example, in a surgical context, a dominant tool may be a clipper that is used to cut tissue of a patient. Further, the dominant tool is typically handled by the dominant hand of the user. The dominant tool is typically non-assistive. For example, dominant tools include cutting tools such as clippers and scissors, burning tools such as bipolar forceps, etc.

Other tools may be referred to as assistive tools in that they assist the user in a primary task using the dominant tool. A non-dominant tool may be an assistive tool such as grasper, which the user may use to grab particular tissue to pull away from tissue to be cut by the clipper. Other assistive tools may include grasper tools, hook tools, irrigation tools, etc.

The dominant tool is typically manipulated by the dominant hand of the user. As such, if system 102 determines the handedness of a particular tool. As such, in some implementations, if system 102 determines that a non-assistive tool is being used by the right hand of the user. System 102 may determine that the right hand is the dominant hand. System 102 may further determine the tool being manipulated by the dominant hand (e.g., the tool on the right) is the dominant tool.

Figure 6:
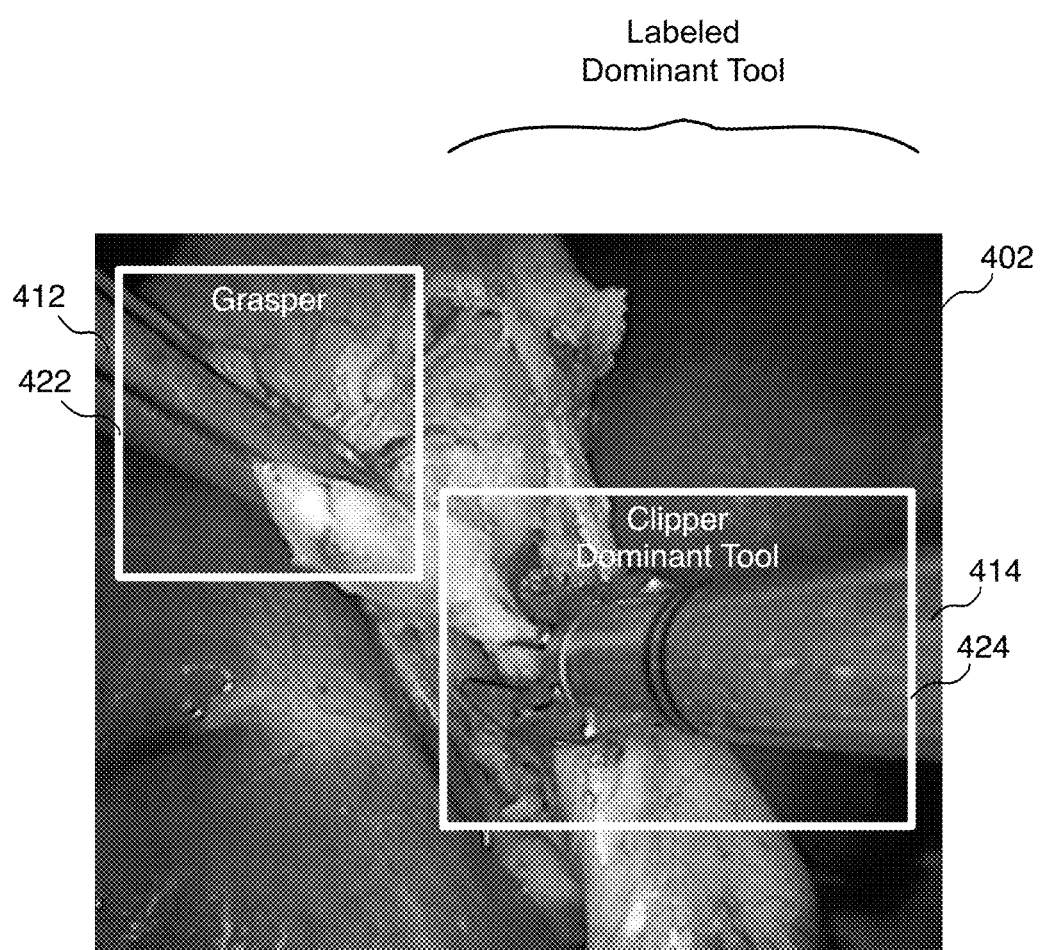
FIG. 6 illustrates example screen shot showing two tools and labels indicating the dominant tool, according to some implementations.

FIG. 6 illustrates example screen shot 600 showing two tools and labels indicating the dominant tool, according to some implementations. Shown is image frame 402 and objects 412 and 414, which are captured and shown in image frame 402. Also shown is box 422, which is a visual indicator that demarcates grasper 412, and box 424, which is a visual indicator that demarcates clipper 414. In various implementations, system 102 labels the tool in image frame 402 as the dominant tool. For example, as shown, system 102 may label tool 414 with text to indicate that tool 414 is the dominant tool.

In some implementations, system 102 may indicated the dominant tool with color coding. For example, system 102 may indicate the dominant tool with a red box or other colored box to highlight the dominant tool.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

Figure 7:
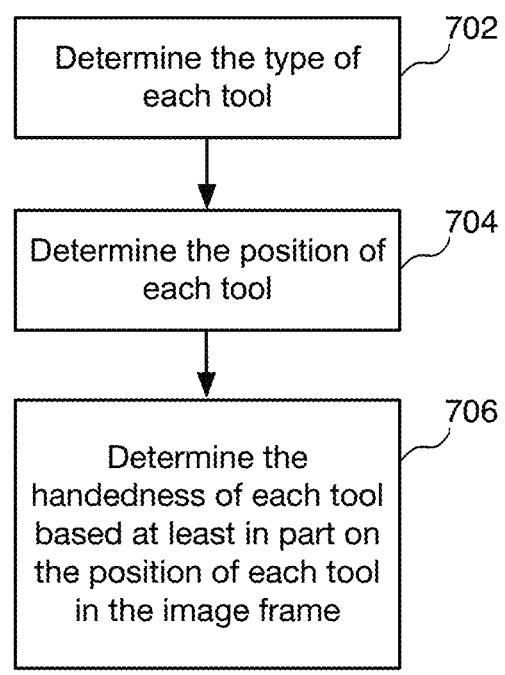
FIG. 7 illustrates an example flow diagram for determining handedness of tools, according to some implementations.

FIG. 7 illustrates an example flow diagram for determining handedness of tools, according to some implementations. A method is initiated at block 702, where the system such as system 102 determines the type of each tool. At block 704, system 102 determines the position of each tool in the image frame. At block 706, system 102 determines the handedness of each tool based at least in part on the position of each tool in the image frame.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

In various implementations, system 102 uses the dominant tool information to provide a natural user interface design with features such as autofocus, automatic warning systems, surgical workflow analysis (e.g., endoscopy, laparoscopy, etc.), and surgical skills assessment. The following example is directed to automatically positioning a camera that is capturing video of tools being used during surgery.

Figure 8:
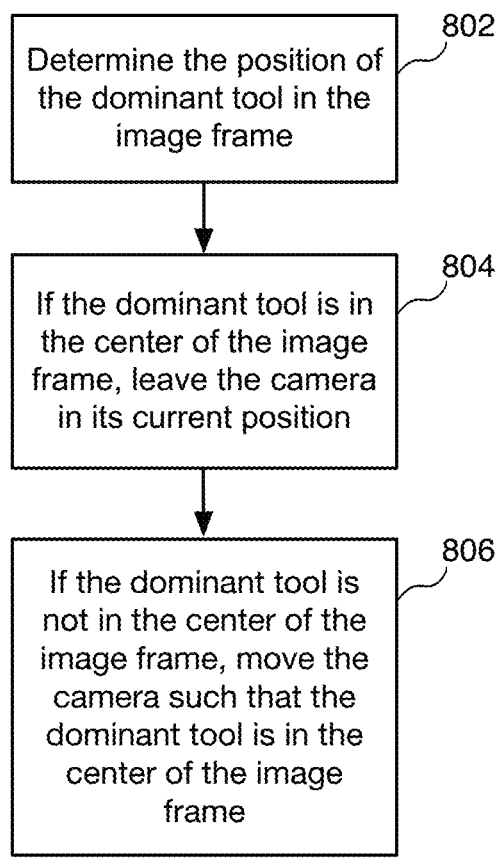
FIG. 8 illustrates an example flow diagram for positioning a camera, according to some implementations.

FIG. 8 illustrates an example flow diagram for positioning a camera, according to some implementations. For example, system 102 may control a camera based at least in part on the determining of the dominant tool. In some embodiments, system 102 alters an image of the dominant tool based at least in part on the determining of the dominant tool. A method is initiated at block 802, where the system such as system 102 determines the position of the dominant tool in the image frame. At block 804, if the dominant tool is in the center of the image frame, system 102 leaves the camera in its current position. At block 806, if the dominant tool is not in the center of the image frame, system 102 moves the camera such that the dominant tool is in the center of the image frame.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

Implementations described herein provide various benefits. For example, implementations determine the handedness of surgical tools used during surgery. Implementations described herein also determine the dominant tool during surgery.

Implementations described herein may be used in various applications in computer☐based assistances for different kinds of surgeries. For example implementations may be applied to procedures involving endoscopy and laparoscopy. Implementations may be used to automatically adjust a camera during surgery (e.g., to place the dominant tool in the center of the image, for autofocusing, etc.). Implementations may be use with robotic arms during surgery. Implementation may also be used to provide warning (e.g., if a tool is too close to a particular part of an organ, etc.).

Figure 9:
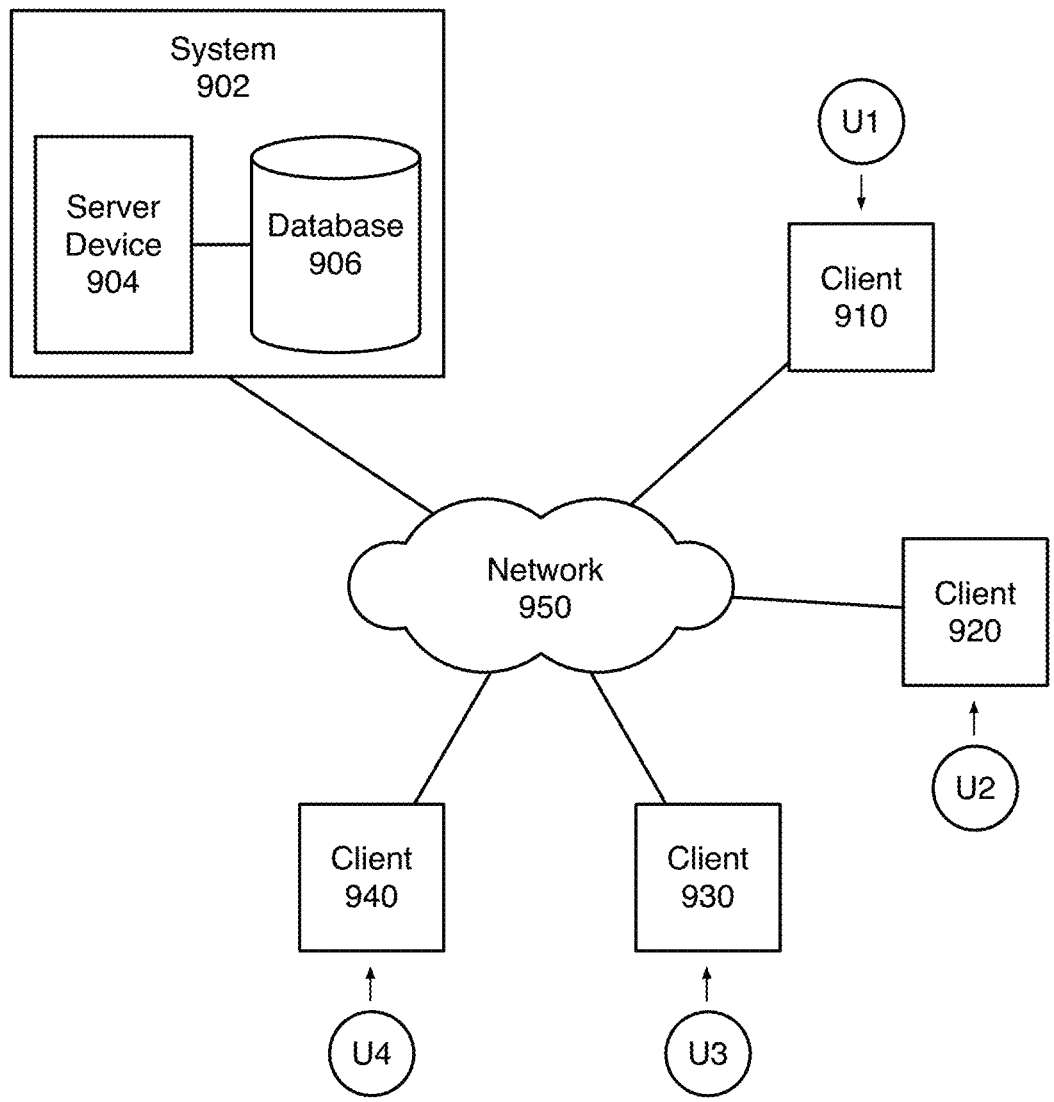
FIG. 9 illustrates a block diagram of an example network environment, which may be used for some implementations described herein.

FIG. 9 illustrates a block diagram of an example network environment 900, which may be used for some implementations described herein. In some implementations, network environment 900 includes a system 902, which includes a server device 904 and a network database 906. Network environment 900 also includes client devices 910, 920, 930, and 940, which may communicate with each other directly or via system 902. Network environment 900 also includes a network 950.

For ease of illustration, FIG. 9 shows one block for each of system 902, server device 904, and network database 906, and shows four blocks for client devices 910, 920, 930, and 940. While some implementations are description are described in the context of one client device being used to view a video of a surgery procedure (e.g., one surgeon viewing the video), these implementations and others may apply to multiple client devices. For example, there may be other physicians, and/or other clinicians, and/or students viewing the video.

Blocks 902, 904, and 906 may represent multiple systems, server devices, and network databases. Also, there may be any number of client devices. In other implementations, network environment 900 may not have all of the components shown and/or may have other elements including other types of elements instead of, or in addition to, those shown herein. In various implementations, users U1, U2, U3, and U4 may interact with each other or with system 902 using respective client devices 910, 920, 930, and 940.

In the various implementations described herein, a processor of system 902 and/or a processor of any client device 910, 920, 930, and 940 causes the elements described herein (e.g., information, etc.) to be displayed in a user interface on one or more display screens.

Implementations may apply to any network system and/or may apply locally for an individual user. For example, implementations described herein may be implemented by system 902 and/or any client device 910, 920, 930, and 940. System 902 may perform the implementations described herein on a stand-alone computer, tablet computer, smartphone, etc. System 902 and/or any of client devices 910, 920, 930, and 940 may perform implementations described herein individually or in combination with other devices.

Figure 10:
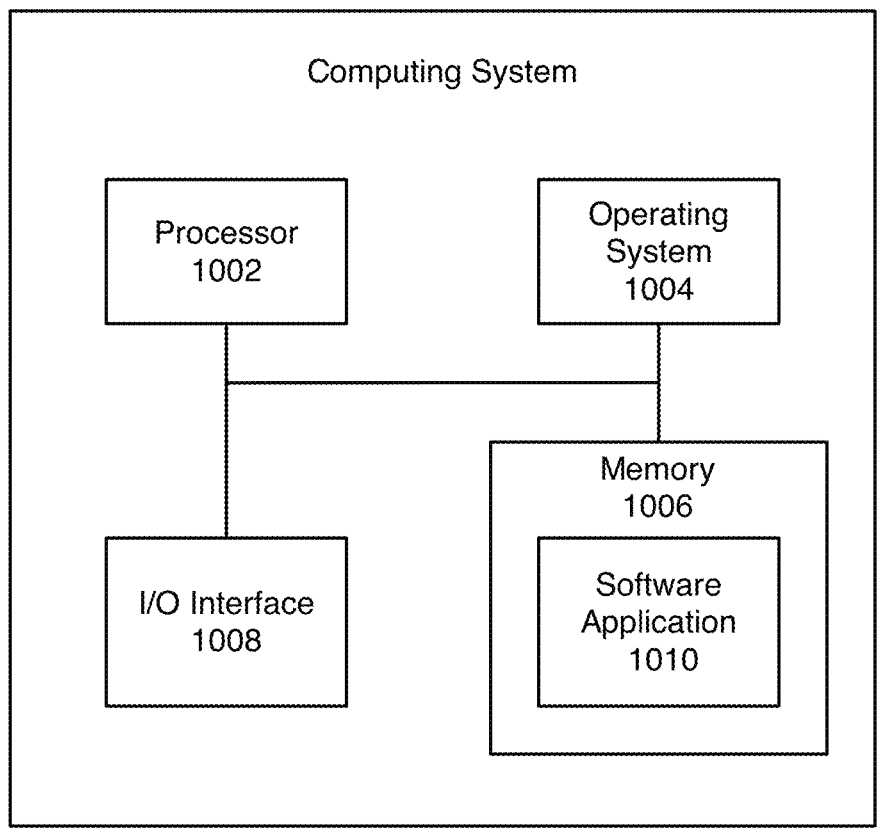
FIG. 10 illustrates a block diagram of an example computing system, which may be used for some implementations described herein.

FIG. 10 illustrates a block diagram of an example computing system 1000, which may be used for some implementations described herein. For example, computing system 1000 may be used to implement system 102 of FIG. 1 and/or system 902 of FIG. 9, as well as to perform implementations described herein. In some implementations, computing system 1000 may include a processor 1002, an operating system 1004, a memory 1006, and an input/output (I/O) interface 1008. In various implementations, processor 1002 may be used to implement various functions and features described herein, as well as to perform the method implementations described herein. While processor 1002 is described as performing implementations described herein, any suitable component or combination of components of computing system 1000 or any suitable processor or processors associated with computing system 1000 or any suitable system may perform the steps described. Implementations described herein may be carried out on a user device, on a server, or a combination of both.

Computing system 1000 also includes a software application 1010, which may be stored on memory 1006 or on any other suitable storage location or computer-readable medium. Software application 1010 provides instructions that enable processor 1002 to perform the implementations described herein and other functions. Software application may also include an engine such as a network engine for performing various functions associated with one or more networks and network communications. The components of computing system 1000 may be implemented by one or more processors or any combination of hardware devices, as well as any combination of hardware, software, firmware, etc.

For ease of illustration, FIG. 10 shows one block for each of processor 1002, operating system 1004, memory 1006, I/O interface 1008, and software application 1010. These blocks 1002, 1004, 1006, 1008, and 1010 may represent multiple processors, operating systems, memories, I/O interfaces, and software applications. In various implementations, computing system 1000 may not have all of the components shown and/or may have other elements including other types of components instead of, or in addition to, those shown herein.

Although the description has been described with respect to particular embodiments thereof, these particular embodiments are merely illustrative, and not restrictive. Concepts illustrated in the examples may be applied to other examples and implementations.

In various implementations, software is encoded in one or more non-transitory computer-readable media for execution by one or more processors. The software when executed by one or more processors is operable to perform the implementations described herein and other functions.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a non-transitory computer-readable storage medium (also referred to as a machine-readable storage medium) for use by or in connection with the instruction execution system, apparatus, or device. Particular embodiments can be implemented in the form of control logic in software or hardware or a combination of both. The control logic when executed by one or more processors is operable to perform the implementations described herein and other functions. For example, a tangible medium such as a hardware storage device can be used to store the control logic, which can include executable instructions.

Particular embodiments may be implemented by using a programmable general purpose digital computer, and/or by using application specific integrated circuits, programmable logic devices, field programmable gate arrays, optical, chemical, biological, quantum or nanoengineered systems, components and mechanisms. In general, the functions of particular embodiments can be achieved by any means as is known in the art. Distributed, networked systems, components, and/or circuits can be used. Communication, or transfer, of data may be wired, wireless, or by any other means.

A "processor" may include any suitable hardware and/or software system, mechanism, or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems. A computer may be any processor in communication with a memory. The memory may be any suitable data storage, memory and/or non-transitory computer-readable storage medium, including electronic storage devices such as random-access memory (RAM), read-only memory (ROM), magnetic storage device (hard disk drive or the like), flash, optical storage device (CD, DVD or the like), magnetic or optical disk, or other tangible media suitable for storing instructions (e.g., program or software instructions) for execution by the processor. For example, a tangible medium such as a hardware storage device can be used to store the control logic, which can include executable instructions. The instructions can also be contained in, and provided as, an electronic signal, for example in the form of software as a service (SaaS) delivered from a server (e.g., a distributed system and/or a cloud computing system).

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

What is claimed is:

1. A system comprising:
one or more processors; and
logic encoded in one or more non-transitory computer-readable storage media for execution by the one or more processors and when executed operable to perform operations comprising:
receiving at least one image frame;
detecting one or more objects in the at least one image frame;
classifying the one or more objects into one or more tool classifications, wherein the one or more objects are one or more tools;
determining if each tool of the one or more tools is non-assistive based on the one or more tool classifications;
determining a handedness of the one or more tools; and
determining a dominant tool from the one or more tools based at least in part on the dominant tool being determined as non-assistive and based at least in part on the handedness of the one or more tools.

2. The system of claim 1, wherein the one or more tool classifications indicate if a particular tool is assistive or non-assistive.

3. The system of claim 1, wherein the one or more tool classifications indicate tool functions.

4. The system of claim 1, wherein the logic when executed is further operable to perform operations comprising:
generating a visual indicator for the one or more tools; and
demarcating each of the one or more tools in the at least one image frame.

5. The system of claim 1, wherein the logic when executed is further operable to perform operations comprising labeling each tool in the at least one image frame with a type of tool.

6. The system of claim 1, wherein the logic when executed is further operable to perform operations comprising performing the determining of the dominant tool in real-time.

7. The system of claim 1, wherein the logic when executed is further operable to perform operations comprising controlling a camera based at least in part on the determining of the dominant tool.

8. A non-transitory computer-readable storage medium with program instructions stored thereon, the program instructions when executed by one or more processors are operable to perform operations comprising:
receiving at least one image frame;
detecting one or more objects in the at least one image frame;
classifying the one or more objects into one or more tool classifications, wherein the one or more objects are one or more tools;
determining if each tool of the one or more tools is non-assistive based on the one or more tool classifications;
determining a handedness of the one or more tools; and
determining a dominant tool from the one or more tools based at least in part on the dominant tool being determined as non-assistive and based at least in part on the handedness of the one or more tools.

9. The computer-readable storage medium of claim 8, wherein the one or more tool classifications indicate types of tools.

10. The computer-readable storage medium of claim 8, wherein the one or more tool classifications indicate tool functions.

11. The computer-readable storage medium of claim 8, wherein the instructions when executed are further operable to perform operations comprising:
generating a visual indicator for the one or more tools; and
demarcating each of the one or more tools in the at least one image frame.

12. The computer-readable storage medium of claim 8, wherein the instructions when executed are further operable to perform operations comprising labeling each tool in the at least one image frame with a type of tool.

13. The computer-readable storage medium of claim 8, wherein the instructions when executed are further operable to perform operations comprising performing the determining of the dominant tool in real-time.

14. The computer-readable storage medium of claim 8, wherein the instructions when executed are further operable to perform operations comprising controlling a camera based at least in part on the determining of the dominant tool.

* * * * *